(12) United States Patent
Hitce et al.

(10) Patent No.: US 11,058,619 B2
(45) Date of Patent: Jul. 13, 2021

(54) CARBOXYLATED POLYPHENOL DERIVATIVES AND THEIR COSMETIC USE

(71) Applicant: L'ORÉAL, Paris (FR)

(72) Inventors: Julien Hitce, Aulnays-sous-Bois (FR); Maria Dalko, Aulnays-sous-Bois (FR)

(73) Assignee: L'ORÉAL, Paris (FR)

( * ) Notice: Subject to any disclaimer, the term of this patent is extended or adjusted under 35 U.S.C. 154(b) by 0 days.

(21) Appl. No.: 16/806,496

(22) Filed: Mar. 2, 2020

(65) Prior Publication Data
US 2020/0197275 A1   Jun. 25, 2020

Related U.S. Application Data

(62) Division of application No. 16/088,105, filed as application No. PCT/EP2017/057741 on Mar. 31, 2017.

(30) Foreign Application Priority Data

Mar. 31, 2016  (FR) ...................................... 1652777

(51) Int. Cl.
| | |
|---|---|
| A61K 8/37 | (2006.01) |
| A61K 8/368 | (2006.01) |
| A61Q 19/02 | (2006.01) |
| A61Q 19/08 | (2006.01) |
| C07C 65/105 | (2006.01) |
| C07C 65/19 | (2006.01) |
| C07C 69/94 | (2006.01) |
| A61Q 19/00 | (2006.01) |

(52) U.S. Cl.
CPC ................ *A61K 8/37* (2013.01); *A61K 8/368* (2013.01); *A61Q 19/004* (2013.01); *A61Q 19/02* (2013.01); *A61Q 19/08* (2013.01); *C07C 65/105* (2013.01); *C07C 65/19* (2013.01); *C07C 69/94* (2013.01)

(58) Field of Classification Search
None
See application file for complete search history.

(56) References Cited

FOREIGN PATENT DOCUMENTS

WO    WO 03055444 A2    7/2003

OTHER PUBLICATIONS

Plasch, K.; Resch, V.; Hitce, J.; Poplonski, J.; Faber, K.; Glueck, S.M. Regioselective Enzymatic Carboxylation of Bioactive (Poly) phenols. Adv. Synth. Catal. 2017, 359, p. 959-965. (Year: 2017).*
Takahashi, M., et al., "Direct Measurement of Crosslinks, Pyridinoline, Deoxypyridinoline, and Pentosidine, in the Hydrolysate of Tissues Using High-Performance Liquid Chromatography", Analytical Biochemistry, vol. 232, 1995, pp. 158-162.
Tarsio, J.F., et al., "Nonenzymatic Glycation of Fibronectin and Alterations in the Molecular Association of Cell Matrix and Basement Membrane Components in Diabetes Mellitus", Diabetes, vol. 34, May 1985, pp. 477-484.
Tarsio, J.F., et al., "Molecular Mechanisms in Basement Membrane Complications of Diabetes: Alterations in Heparin, Laminin, and Type IV Collagen Association", Diabetes, vol. 37, May 1988, pp. 532-539.
Sato, M., et al., "Enzymatic Carboxylation of Hydroxystilbenes by the γ-Resorcylic Acid Decarboxylase from *Rhizobium radiobacter* WU-0106 under Reverse Reaction Conditions", Journal of Molecular Catalysis B; Enzymatic, vol. 122, 2015, p. 348-352.

* cited by examiner

*Primary Examiner* — Jessica Worsham
(74) *Attorney, Agent, or Firm* — Oblon, McClelland, Maier & Neustadt, L.L.P.

(57) ABSTRACT

A subject matter of the present invention is the cosmetic use of at least one compound of formula (I):

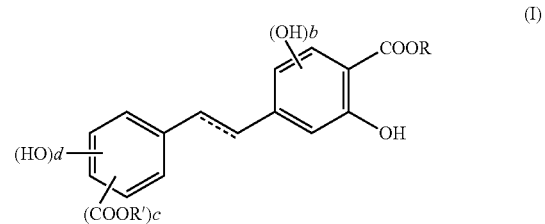

in which:

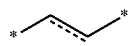

denotes a divalent radical chosen from a carbon-carbon single bond *—$CH_2$—$CH_2$—* or double bond *—CH═CH—*, of Z or E configuration or their mixtures, b=0 or 1, c=0 or 1, d=0, 1 or 2, and R and R' independently denote a hydrogen atom, a linear $C_1$-$C_6$ alkyl radical or a branched $C_3$-$C_6$ alkyl radical, to treat and/or prevent signs of aging and/or of photoaging of keratinous substances, preferably of the skin, and/or to depigment, lighten and/or whiten keratinous substances, preferably the skin.
The present invention also relates to novel compounds and to a corresponding cosmetic method.

11 Claims, No Drawings

CARBOXYLATED POLYPHENOL DERIVATIVES AND THEIR COSMETIC USE

CROSS REFERENCE TO RELATED APPLICATIONS

This application is a divisional application of prior U.S. application Ser. No. 16/088,105, filed Sep. 25, 2018, the disclosure of which in incorporated in its entirety by reference herein. U.S. application Ser. No. 16/088,105 is the national stage of PCT/EP2017/057741, filed Mar. 31, 2017, the disclosure of which in incorporated in its entirety by reference herein. U.S. application Ser. No. 16/088,105 claims priority to French Application No. 1652777, filed Mar. 31, 2016, the disclosure of which in incorporated in its entirety by reference herein.

The present invention relates to the field of the treatment of the signs of aging of keratinous substances, in particular human keratinous substances, and more particularly of the skin, and also to the field of the depigmentation and/or lightening and/or whitening of the skin.

More particularly, the invention relates to the cosmetic use of at least one compound of formula (I) as defined below, namely a carboxylated polyphenol derivative, for the purpose of decreasing and/or delaying the signs of aging of keratinous substances and in particular of the skin and/or also for the purpose of depigmenting and/or lightening and/or whitening the skin. The invention also relates to novel compounds of formulae (III) to (V) as defined below.

Human skin is made up of three compartments, namely a superficial compartment, which is the epidermis, the dermis, and a deep compartment, which is the hypodermis.

The dermis provides the epidermis with a solid support. It is also its nourishing element. It is mainly constituted of fibroblasts and an extracellular matrix (ECM).

This extracellular matrix is constituted of various macromolecules responsible for the mechanical strength of the skin, for its suppleness, for its tonicity and for its elasticity, and also for the important physiological functions (moisturization, thermoregulation and regulation of skin permeability). Among these macromolecules are in particular collagens, glycosaminoglycanes (GAG), elastin and glycoconjugates (glycoproteins and proteoglycans).

Collagens represent 70% of the ECM proteins. In the skin, numerous types of collagen constitute the ECM, including in particular the interstitial collagens (type I, II, III collagens) of fibrillar structure, produced essentially by the fibroblasts, and responsible for the cohesion, the rigidity and the mechanical strength, the collagens of the basal lamina (type IV collagens) synthesized by the adjacent cells and in the skin by the keratinocytes and which play in particular a mechanical role, and the collagens which form fibrils for anchoring of the basal membrane (dermis-epidermis link) expressed by the epidermal keratinocytes (type VII collagens).

It is also known that collagen synthesis begins with the assembly of procollagen units. For example, for the synthesis of collagen type I, these are units of procollagen type I (also called Pro-Coll 1).

Naturally, collagen fibers are constantly renewed, but this renewal decreases with age, which leads to thinning of the dermis.

The glycosaminoglycans or glycosaminoglycans (GAGs) are optionally sulphated linear chains composed of the repetition of a base diholoside always containing a hexosamine (glucosamine or galactosamine) and another ose (glucuronic acid, iduronic acid or galactose). The glucosamine is either N-sulfated or N-acetylated. In contrast, galactosamine is always N-acetylated. In addition, there may be O-bonded sulfates on hexosamine, uronic acid and galactose.

The strong anionic nature of GAGs is explained by the presence of carboxylate groups in hexuronic acids (glucuronic acid and iduronic acid) and O- and N-linked sulfate groups.

GAGs are forming an important component of connective tissue. The GAG chains may be covalently linked to a protein to form proteoglycans.

GAGs are naturally present in the skin, in the extracellular matrix of the dermis.

GAGs have long been referred to as acid mucopolysaccharides due to their high water retention capacity, their carbohydrate nature and their acidic character from their multiple negative charges.

One of the major GAG is hyaluronic acid or hyaluronan (HA).

Hyaluronic acid or hyaluronan (HA) is the main GAG of the dermis, the latter containing half of HA of the organism. It is a polymer of disaccharides themselves composed of D-glucuronic acid and D-N-acetylglucosamine, linked together by alternating beta-1,4 and beta-1,3 glycosidic bonds. It has a very high intrinsic viscosity, ensuring the assembly of the various elements of the connective tissue by formation of supramolecular complexes. Hyaluronic acid is known as being an important constituent of extracellular matrix, playing major role for instance in mechanical properties of dermis.

In addition, glycation is a non-enzymatic process involving a saccharide (glucose or ribose) which reacts via the Maillard reaction with an amine group of an amino acid residue (for instance lysine), particularly an amino acid residue of a protein, to form a Schiffs base. This base, after an "Amadori" molecular rearrangement, may lead, via a succession of reactions, to bridging, particularly intermolecular bridging, for instance of pentosidine type.

This phenomenon is characterized by the appearance of glycation products, the content of which increases uniformly as a function of age. Glycation products are, for example, pyrraline, carboxymethyllysine, pentosidine, crossline, $N^e$(2-carboxyethyl)lysine (CEL), glyoxal-lysine dimer (GOLD), methylglyoxal-lysine dimer (MOLD), 3DG-ARG imidazolone, versperlysines A, B, C, threosidine, or advanced glycosylation end products (or AGEs).

The glycation of proteins is therefore a universal phenomenon, well known in the skin, particularly at the level of the collagen fibers. The glycation of collagen in fact increases uniformly with age, leading to a uniform increase in the content of glycation products in the skin.

Without wishing to introduce any one theory of aging of the skin, it should be noted that it has been possible to demonstrate during skin aging other changes in collagen which might also be a consequence of glycation, such as a decrease in heat denaturation, an increase in resistance to enzymatic digestion and an increase in intermolecular bridging (Tanaka S. et al., 1988, J. Mol. Biol., 203, 495-505; Takahashi M. et al., 1995, Analytical Biochemistry, 232, 158-162). Furthermore, glycation-mediated changes in certain constituents of the basal membrane such as collagen IV, laminin and fibronectin were able to be demonstrated (Tarsio J F. et al., 1985, Diabetes, 34, 477-484; Tarsio J F. et al., 1988, Diabetes, 37, 532-539; Sternberg M. et al., 1995, C. R. Soc. Biol., 189, 967-985).

It is thus understood that, in the course of aging of the skin, the physicochemical properties of collagen become modified and collagen becomes more difficult to dissolve and more difficult to degrade. A stiffening of the tissues follows, resulting essentially in a loss of skin tonicity.

Moreover, the skin changes due to intrinsic aging are the consequence of genetically programmed senescence in which endogenous factors are involved. This intrinsic aging causes in particular a slowing of skin cell renewal, which is essentially reflected by the occurrence of detrimental clinical modifications, such as a reduction in subcutaneous adipose tissue and the appearance of fine wrinkles or fine lines, and by histopathological changes, such as an increase in the number and thickness of elastic fibers, a loss of vertical fibers of the elastic tissue membrane, and the presence of large irregular fibroblasts in the cells of this elastic tissue. The epidermis, which constitutes the upper layer of the skin, is undergoing constant regeneration. The epidermis is constituted of several layers of cells, the deepest of which is the basal layer constituted of undifferentiated cells. Over time, these cells will differentiate and migrate to the surface of the epidermis while constituting the various layers thereof, until they form, at the surface of the epidermis, the corneocytes which are dead cells that are eliminated by the natural phenomenon of desquamation. This loss at the surface is compensated for by the migration of cells from the basal layer toward the surface of the epidermis. There is perpetual renewal of the skin. The epidermis is therefore constantly engaged in producing new keratinocytes to compensate for the continuous loss of epidermal cells at the horny layer. However, in the course of aging, a decrease in the number of cells in the proliferation phase, and consequently a decrease of the live epidermal layers, may be observed physiologically.

The homeostasis of the skin, and in particular of the epidermis, results from a finely regulated balance between the processes of proliferation and of differentiation of the skin cells. These processes of proliferation and differentiation are entirely regulated: they participate in the renewal and/or regeneration of the skin and lead to the maintenance of a constant thickness of the skin, and in particular of a constant thickness of the epidermis. This homeostasis of the skin also participates in maintaining the mechanical properties of the skin.

However, this homeostasis of the skin may be detrimentally affected by certain physiological factors (age, menopause, hormones, and the like) or environmental factors (UV stress, oxidative stress, irritant stress, and the like).

The proliferative cells are metabolically very active and are sensitive to these deleterious factors (intrinsic or environmental), with, as a consequence on the epidermis, a reduction in their amount. It is thus important to preserve these cells in order to contribute towards delaying the onset of the signs of aging.

The cell vitality of keratinocytes may be reduced in particular in the context of aging or because of oxidative stress (for example solar, i.e. UV, radiation, radiation in the visible range, infrared radiation), because of the epidermis being attacked by toxins or metabolites of the microflora, or, more generally, during chronological aging. The capacity for renewal and differentiation of the keratinocytes is reduced and the homeostasis of structures dependent thereon, such as the barrier function of the epidermis, is detrimentally affected.

When the regenerative potential of the epidermis becomes smaller: the cells of the basal layer divide less actively, leading in particular to a slowing-down and/or decrease in epidermal renewal. Consequently, the cell renewal no longer compensates for the loss of cells removed at the surface, leading to atrophy of the epidermis and/or a reduction in skin thickness.

Detrimental changes in epidermal homeostasis are also reflected by a dull and/or off-color appearance of the skin complexion.

Detrimental change of the barrier function is manifested by various signs depending on the localization: hyperkeratosis, thin epidermis, surface wrinkles.

The signs associated with a detrimental change of the cellular vitality of the epidermis thus concern not only its structure, but also its homeostasis. The resistance to stress of the epidermis and its capacity for regeneration are reduced. If the skin barrier of an elderly person is compared with that of a young adult, the differences do not appear at first sight: the thickness of the horny layer and the composition of its lipids are not necessarily detrimentally changed, and the barrier function is preserved. The deficiencies of the elderly skin barrier appear under mechanical stress or during exposure to irritant factors: the barrier of an elderly epidermis degrades more rapidly and its function recovers less quickly. On a daily basis, actions such as alcoholic disinfection or contact with lemon juice then cause discomfort, and dry air is poorly tolerated, whereas young skin tolerates this without any problem.

These esthetic signs, such as wrinkles or fine lines, are such that there is a need in cosmetics for compounds which act on the skin to improve the cellular vitality when it is detrimentally affected.

AMPK is present in all the cells of the body and plays the role of energy gauge therein. AMPK (or 5'-adenosine monophosphate activated protein kinase) is a heterotrimeric enzyme composed of a catalytic subunit $\alpha$ with kinase activity and of two regulatory subunits $\beta$ and $\gamma$. The activity of AMPK depends on the variation in the AMP/ATP ratio which characterizes the energy level of the cell (ATP being hydrolyzed to give AMP in order to "deliver" the energy required for the various biochemical processes of the cell). It is present in two forms, phosphorylated or non-phosphorylated, the phosphorylated form being the active form.

When it is activated in response to an energy demand or to a stress of the cell, AMPK increases the energy-generating processes, such as glycolysis, and it inhibits the non-essential consuming processes, thus enabling cell survival. Preservation of the cellular energy status is involved in maintaining the longevity of the species and combating the signs of aging. Thus, compounds which are capable of increasing the activity of AMPK are at the present time the object of great interest in the treatment of age-related clinical manifestations. The advantage in transposing this approach, validated for the whole body, to the skin in the context of preventing age-related detrimental changes thereto is understood.

The AMPK activity corresponds to the cellular concentration of phosphorylated AMPK. Thus, it is advisable to have the highest possible levels of phosphorylated protein in order to have this high activity.

The role of AMPK in controlling the energy metabolism of the keratinocyte is suspected at the present time Prahl S et al., Biofactors, 2008, 32 (1-4), 245-55); its involvement in the proliferation and differentiation of the keratinocyte has been established (Saha A. K. et al., Biochem. Biophys. Res. Commun., 2006, Oct. 20, 349(2), 519-24).

WO 2004/05098 proposes to modulate the lifetime of any cell or of an organism by controlling the activity of AMPK, and to treat age-related disorders by administering modulators of the AMPK metabolic pathway, without stating whether it involves an activator or an inhibitor.

Saha et al. (Biochem. Biophys. Res. Commun., 2006, 349:519-524) studied the AMPK-regulated growth of keratinocytes and conclude that AMPK activators, such as AICAR, promote the in vitro differentiation of keratinocytes.

Moreover, it is also accepted that extrinsic factors, such as ultraviolet rays, smoking or certain treatments (glucocorticoids, vitamin D and derivatives, for example), also have an effect on the skin and its collagen content.

Thus, prolonged exposure to ultraviolet radiation, particularly to type A and B radiation, has the effect of stimulating the expression of collagenases, particularly of MMP1 (also known as matrix metalloproteinase 1 or else interstitial collagenase), constituting one of the components of photoinduced or non-photoinduced skin aging.

A certain number of active agents have already been proposed for preventing and/or treating the signs of skin aging.

It is thus known to use specific hydroxylated compounds in order to stimulate collagen synthesis and/or the proliferation of fibroblasts of the dermis, as described in the French application FR 2 777 186.

Moreover, as previously mentioned, skin aging may be photoinduced, that is to say that it may be caused following exposure to the sun. This extrinsic aging is then called photoaging or dermatoheliosis.

Conversely, "conventional" aging is sometimes called "chronological aging" or "intrinsic aging".

Keratinous substances, and in particular the skin, are exposed daily to sunlight. In point of fact, it is known that prolonged exposure of keratinous substances, and in particular of the skin, to this polychromatic light is capable of inducing skin disorders or else superficial damage. This is in particular due to the formation of free radicals, reactive oxygen entities such as $O_2^-$ and $HO^·$, which can damage DNA, certain lipids and/or proteins, and more generally which induce cell aging. These reactive entities disrupt biological mechanisms by inducing oxidative stress. This contributes to the development and acceleration of cell degeneration.

The production of reactive oxygen entities therefore causes damage to DNA, to proteins and/or to lipids, and contributes to the acceleration of aging of the cells of the skin in particular.

Thus, the effects of oxidative stress affect cell respiration and result in an accelerated aging of the skin, accompanied in particular by a dull and/or grey complexion, an uneven complexion, a loss of radiance and/or transparency of the skin, the premature formation of wrinkles or fine lines, and a loss of softness, suppleness and elasticity of the skin.

Thus, UV radiation induces a phenomenon termed "photoaging", in particular of the skin, which includes as associated signs the appearance of wrinkles/fine lines, a loss of radiance and an unevenness of the complexion, a loss of firmness, and the appearance of roughness and of yellowing of the skin.

Exposure to the sun induces peroxidation of the surface lipids of the skin and in particular photoinduced peroxidation of lipids of sebaceous origin, such as squalene. This is because it is known that lipids which are at the surface of the skin are continuously subjected to external attacks and in particular the air, atmospheric pollutants and visible radiation and especially ultraviolet (UV) radiation, and that the most exposed to external attacks are those present in the fatty secretions of the skin, such as sebum, which is rich in squalene. The presence in the squalene molecules of six double bonds makes these molecules sensitive to oxidation phenomena. Thus, during prolonged exposure to UV radiation, squalene becomes photoperoxidized to give squalene peroxides. This high production of squalene peroxides causes in particular a series of chain degradations, in particular in and on the skin, giving rise to numerous skin disorders including photoaging.

Numerous agents or treatments for preventing and/or treating photoaging already exist, such as vitamin A, botulinum toxin, skin filling agents, various laser treatments, dermabrasion and peels.

In addition, numerous antioxidants, used in the cosmetics industry for combating free radicals, are already known.

The role of antioxidants is to capture and neutralize free radicals by converting them into subentities, without danger to keratinous substances.

Antioxidants can therefore be used in various fields, such as antiaging cosmetics, and protection against oxidative stress and in particular that caused by exposure to the sun.

Mention may in particular be made of vitamin E (α-tocopherols and isomers), vitamin C (ascorbic acid) and its derivatives, carotenoids, aminoindoles, melatonin, ubiquinone, coenzyme Q, green tea, thiols and their derivatives (glutathione, N-acetylcysteine), oligomeric proanthocyanidins (OPCs), flavonoids, catechins, in particular epicatechin and also its gallic derivatives, polyphenols, such as, for example, tyrosol, hydroxytyrosol, sesamol, carnosol, γ-orizanol, acids such as dihydrolipoic acid, uric acid, ferulic acid, caffeic acid, rosemarinic acid or carnosic acid, and also trans-resveratrol.

Resveratrol is furthermore an active agent of the family of the polyphenols, the effectiveness of which is recognized in antiaging and as antioxidant but the formulation of which requires the use of optimized supports in order to ensure the solubility and the photostability thereof.

However, there remains a constant need to have available new active agents capable of exerting a beneficial cosmetic action with regard to the signs of skin aging, in particular the chronological signs, or of photoaging, and also a protective action for keratinous substances against the effects of UV radiation, in particular for combating free radicals.

It is an object of the present invention to meet this need.

Unless otherwise specified, the term "signs of aging" encompasses intrinsic and extrinsic signs of aging, as defined below.

The term "mechanical properties" of the skin intends to mean the properties of the skin in connection to its extensibility, tonicity, firmness, suppleness and/or elasticity.

In addition to the appearance of cutaneous signs of aging, it is also possible to observe, on the skin, the appearance of a nonuniformity of the complexion which may prove to be troublesome, or also some people may be desirous of modifying their skin tone, for example of lightening it and/or of whitening it.

In particular, at different periods of their lives, some people witness the appearance on the skin and more especially on the hands and the face of darker and/or more highly colored blemishes which give the skin a lack of uniformity. These blemishes are due in particular to a high concentration of melanin in the keratinocytes situated at the surface of the skin.

An overall lightening action on the complexion or flesh tone of the skin may also be desired, without necessarily corresponding to an appearance of blemishes.

The use of inoffensive topical depigmenting substances which are highly effective is very particularly sought after with a view to treating pigment blemishes.

The mechanism of formation of the pigmentation of the skin, that is to say of the formation of melanin, is particularly complex and involves, schematically, the following main stages:

Tyrosine→Dopa Dopaquinone→Dopachrome→Melanin

Tyrosinase (monophenol dihydroxyl phenylalanine: oxygen oxidoreductase EC 1.14.18.1) is the essential enzyme involved in this sequence of reactions. In particular, it catalyzes the conversion reaction of tyrosine to give dopa (dihydroxyphenylalanine), by virtue of its hydroxylase activity, and the conversion reaction of dopa to give dopaquinone, by virtue of its oxidase activity. This tyrosinase acts only when it is in the maturation state under the effect of certain biological factors.

A substance is recognized as depigmenting if it acts directly on the vitality of the epidermal melanocytes where melanogenesis takes place and/or if it interferes with one of the stages of the biosynthesis of melanin, either by inhibiting one of the enzymes involved in melanogenesis or by being inserted as structural analog of one of the chemical compounds in the sequence for the synthesis of melanin, which sequence can then be blocked and thus ensure depigmentation.

Arbutin and kojic acid are known as depigmenting agents for the skin.

Substances have been sought which exhibit an effective depigmenting action, in particular superior to that of arbutin and kojic acid.

The need remains for a novel whitening agent for human skin having an action as effective as those known but not having their disadvantages, that is to say which are nonirritating, nontoxic and/or nonallergizing for the skin and which can be easily formulated, while being stable in a composition, or else alternatively which has a reinforced action so as to be able to be used in a lower amount, which considerably reduces the side effects liable to be observed.

In this regard, the applicant company has discovered, surprisingly and unexpectedly, that the compounds of formula (I) as defined below exhibit a good depigmenting activity, even at low concentration, without showing cytotoxicity.

Thus, according to a first subject matter, the present invention relates to the cosmetic use of at least one compound of formula (I):

(I)

in which:

*$\diagup\!\!\diagdown$* denotes a divalent radical chosen from a carbon-carbon single bond *—$CH_2$—CH—* or double bond *—CH—CH—*, of Z or E configuration or their mixtures, b=0 or 1, c=0 or 1, d=0, 1 or 2, it being understood that, if c=1, then d≥1 and the COOR' group is in the ortho position with respect to a phenol functional group, and R and R' independently denote a hydrogen atom, a linear $C_1$-$C_6$ alkyl radical or a branched $C_3$-$C_6$ alkyl radical, preferably a hydrogen atom, a linear $C_1$-$C_4$ alkyl radical or a branched $C_3$-$C_4$ alkyl radical, one of its stereoisomers and/or solvates and/or one of its salts, to treat and/or prevent signs of aging and/or of photoaging of keratinous substances, preferably of the skin, and/or to depigment, lighten and/or whiten keratinous substances, preferably the skin.

According to a particular embodiment, the present invention is directed to a cosmetic use as defined above, wherein it is directed to combat and/or prevent the signs of aging of the keratinous substances and in particular the skin, and in particular wherein it is directed to improve the mechanical properties of the skin, for example firmness.

As set out below, the cosmetic use of compounds of formulae (II) and (II') as are defined below also forms part of the invention, including for the same applications as described for the compounds of formula (I).

According to a second subject matter, the present invention relates to a compound of formula (III):

(III)

in which:

c=0 or 1, it being understood that, if c=1, then the COOR' group is in the ortho position with respect to a phenol functional group, and R and R' independently denote a hydrogen atom, a linear $C_1$-$C_6$ alkyl radical or a branched $C_3$-$C_6$ alkyl radical, preferably a hydrogen atom, a linear $C_1$-$C_4$ alkyl radical or a branched $C_3$-$C_4$ alkyl radical, one of its stereoisomers and/or solvates and/or one of its salts.

As set out below, a compound of formula (III') as defined below also forms part of the invention.

According to a third subject matter, the present invention relates to a compound of formula (IV):

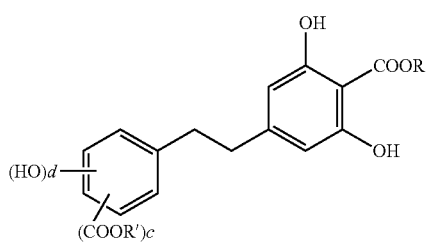

in which:
c=0 or 1,
d=0, 1 or 2,
it being understood that, if c=1, then d≥1 and the COOR' group is in the ortho position with respect to a phenol functional group, and
R and R' independently denote a hydrogen atom, a linear $C_1$-$C_6$ alkyl radical or a branched $C_3$-$C_6$ alkyl radical, preferably a hydrogen atom, a linear $C_1$-$C_4$ alkyl radical or a branched $C_3$-$C_4$ alkyl radical, one of its stereoisomers and/or solvates and/or one of its salts.

According to a fourth subject matter, the present invention also relates to a compound of formula (V):

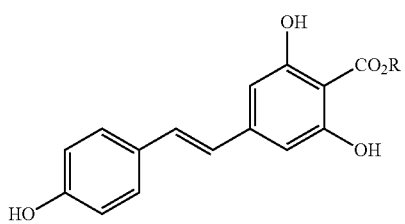

in which:
R denotes a linear $C_1$-$C_6$ alkyl radical or a branched $C_3$-$C_6$ alkyl radical, preferably a linear $C_1$-$C_4$ alkyl radical or a branched $C_3$-$C_4$ alkyl radical, one of its stereoisomers and/or solvates and/or one of its salts.

Another subject matter of the present invention is a composition, preferably a cosmetic composition, comprising, in a physiologically acceptable medium, at least one compound of formula (III), (III'), (IV) or (V) as defined above.

The invention also relates to the cosmetic use of at least one of the compounds of formula (III), (III'), (IV) or (V), of their stereoisomers and/or solvates and/or one of their salts.

Another subject matter of the present invention is a method for the cosmetic treatment of keratinous substances, in particular the skin, comprising the application, to the keratinous substances, of a composition, preferably a cosmetic composition, comprising at least one compound of formula (I), (II), (II'), (III), (III'), (IV) or (V), as defined above and below.

The present invention also relates to a method for the nontherapeutic cosmetic treatment of keratinous substances as defined above, for treating and/or preventing signs of skin aging and/or for protecting keratinous substances, in particular the skin, from the effects of UV radiation.

Another subject matter of the invention is a method for the nontherapeutic cosmetic treatment of keratinous substances as defined above, for depigmenting, lightening and/or whitening keratinous substances, in particular the skin.

Finally, the invention is targeted at a method for the cosmetic treatment of keratinous substances as claimed in the preceding claim, for treating and/or preventing signs of skin aging and/or for protecting keratinous substances, in particular the skin, from the effects of UV radiation and/or for depigmenting, lightening and/or whitening keratinous substances, preferably the skin, in particular for combating and/or preventing the signs of aging of keratinous substances, preferably the skin.

"Keratinous substances" is understood to mean, within the meaning of the present invention, the skin, whether the skin of the body, of the face, of the neck, of the hands or also of the armpits, the lips and the mucus membranes.

"Cosmetic use" is understood to mean, within the meaning of the invention, a nontherapeutic use.

As emerges from the following, the cosmetic use according to the first aspect of the present invention is thus targeted at alleviating or preventing the effects of aging of keratinous substances, and more particularly of the skin, whether it concerns:
intrinsic aging, being a matter for antiaging activity, which, as found above, results from a genetically programmed senescence where endogenous factors are involved, or
extrinsic aging and in particular photoinduced aging, being a matter for photoprotective activity, which is brought about subsequent to exposure to the sun.

Intrinsic Aging—Antiaging Activity

In the context of the present invention, the nontherapeutic cosmetic use, for treating and/or preventing signs of intrinsic aging of keratinous substances, preferably skin aging, may be particularly intended for the prevention and/or the treatment of intrinsic aging of the skin, such as the skin of the face, of the neck, of the body and of the hands and more preferably the skin of the face or of the neck.

Said intrinsic aging may in particular be related to glycation, to cutaneous homeostasis and/or to an increase in the AMPK activity.

One way of reversing the cutaneous homeostasis is to maintain the level of hyaluronic acid sufficient in the extracellular matrix. This could be done with a compound by the stimulation of the expression of the HAS3 marker by keratinocytes, which is the gene coding for hyaluronic acid synthase.

Thus, according to another embodiment, the invention concerns the use of a compound of formula (I), (II), (II'), (III), (III'), (IV) or (IV') as defined above for the activation of the HAS3 marker by keratinocytes in skin.

According to a further embodiment, the invention is directed to the cosmetic use of a compound of formula (I), (II), (II'), (III) or (III') as defined above for improving skin firmness.

It is also intended to target in particular any modification of the external appearance of the skin due to chronological aging, which is manifested, for example, by wrinkles and fine lines, withered skin, flaccid skin, thinned skin, dull, lifeless skin, or lack of elasticity and/or of tone of the skin.

Thus, the present invention relates to the prevention and/or treatment of wrinkles and/or fine lines and/or crevices, and of thinning of the skin.

According to the present invention, "treatment of wrinkles and/or fine lines" is understood to mean the fact of softening wrinkles and/or fine lines, or reducing the appearance of wrinkles and/or fine lines.

In addition, the compounds in accordance with the invention make it possible to combat the loss of firmness and/or of elasticity and/or of tonicity and/or of suppleness and/or the slackening of the skin, and also the radiance of the complexion.

Thus, the present invention relates to the improvement of the firmness of the skin, in particular of mature and/or wrinkled skin, and/or the radiance of the complexion.

The present invention is also targeted at protecting a method for the nontherapeutic cosmetic treatment of the skin for treating and/or preventing signs of skin aging, in particular chronological aging, comprising at least one stage consisting in applying, to the skin, a cosmetic composition comprising at least one compound in accordance with the present invention, in particular of formula (I), (II), (II'), (III), (III'), (IV) or (V).

Extrinsic Aging, in Particular Photoinduced Aging—Photoprotective Activity

For the purposes of the present description, extrinsic aging is caused by physical or chemical attacks from the environment and mainly by UV radiation. Physical attacks from the environment include extreme temperatures.

Thus, in the context of the present invention, the present invention is also targeted at protecting the nontherapeutic cosmetic use of a composition containing, in a physiologically acceptable medium, at least one compound of formula (I), (II), (II'), (III), (III'), (IV) or (V) for protecting the skin from an oxidative stress caused by exposure of the skin to UV radiation, in particular for protecting the skin from an oxidative stress caused by repeated daily and/or prolonged exposure to UV radiation.

Depigmentation

The invention also relates to the nontherapeutic cosmetic use of at least one compound of formula (I), (II), (II'), (III), (III'), (IV) or (V), as defined above and below, as whitening, lightening and/or depigmenting agent for keratinous substances, in particular for the skin.

The compounds in accordance with the invention, namely the compounds of formulae (I), (II), (II'), (III), (III'), (IV) and (V) as defined below, make it possible to effectively depigment and/or lighten, indeed even to whiten, the skin of human beings. They can thus be intended to lighten overall the complexion or flesh tone of the skin. They can also be intended to be applied to the skin of individuals exhibiting brownish pigmentation blemishes or blemishes due to aging, or to the skin of individuals desiring to combat the appearance of a brownish color originating from melanogenesis.

Compounds of formula (I) Used According to the Invention

As already mentioned, the invention relates to the nontherapeutic cosmetic use, as agent for treating and/or preventing signs of skin aging, and/or as a photoprotective agent, in particular as an antioxidant, and/or for depigmenting, lightening and/or whitening keratinous substances, preferably the skin, of a composition containing, in a physiologically acceptable medium, at least one compound of formula (I) defined above and/or at least one of its solvates and/or of its stereoisomers.

Within the meaning of the invention, a $C_1$-$C_x$ alkyl radical is an alkyl group comprising from 1 to x carbon atoms, in particular from 1 to 6 carbon atoms or also from 1 to 4 carbon atoms, that is to say that the alkyl group may comprise, for example, 1, 2, 3, 4, 5 or 6 carbon atoms. Mention may be made, as examples of alkyl groups, of the methyl, ethyl, propyl, isopropyl, butyl, isobutyl, tert-butyl, pentyl or hexyl groups.

Preferably, the isomers according to the invention are stereoisomers, in particular enantiomers, diastereoisomers, and also their mixtures, including racemic mixtures.

According to a preferred alternative form, the compounds of formula (I) are chosen from the diastereoisomers of E (trans) configuration.

The acceptable solvates of the compounds of formula (I) comprise conventional solvates. Mention may be made, by way of example, of the solvates due to the presence of solvents. Mention may be made, by way of example, of the solvates due to the presence of water or of linear or branched alcohols, such as ethanol or isopropanol.

The salts of the compounds of formulae (I), (II), (II'), (III), (IV) and (V) as defined below are organic and/or inorganic cations. They can be chosen from metal cations, for example aluminum ($Al^{3+}$), zinc ($Zn^{2+}$), manganese ($Mn^{2+}$) or copper ($Cu^{2+}$); alkali metal cations, for example lithium ($Li^+$), sodium ($Na^+$) or potassium ($K^+$); and alkaline earth metal cations, for example calcium ($Ca^{2+}$) or magnesium ($Mg^{2+}$). They can also be cations of formula or organic cations of formula $NHX_3^+$, $NX_3$ denoting an organic amine, the X radicals being identical or different, it being possible for two or three X radicals to form, in pairs, a ring with the nitrogen atom which carries them or it being possible for $NX_3$ to denote an aromatic amine. The organic amines denote in particular alkylamines, such as, for example, methylamine, dimethylamine, trimethylamine, triethylamine or ethylamine; hydroxyalkylamines, such as, for example, 2-hydroxyethylamine, bis(2-hydroxyethyl)amine or tri(2-hydroxyethyl)amine; cycloalkylamines, such as, for example, bicyclohexylamine or glucamine, piperidine; pyridines and analogs, for example collidine, quinine or quinoline; and amino acids having a basic nature, such as, for example, lysine or arginine, the number and the nature of the cations depending on the valency of these cations compared with the anionic part in order for the salts of compounds of formula (I) to be neutral compounds overall. In other words, when one at least of the radicals carried by one at least of the aromatic rings of the compounds of formula (I), (II), (II'), (III), (III'), (IV) or (V) is anionic, the electrical neutrality of the compounds of formula (I), (II), (II'), (III), (III'), (IV) or (V) is provided by one or more identical or different cations defined above.

This definition of the salts is valid for all of the compounds in accordance with the invention, whatever the compounds of formula (I), (II), (II'), (III), (III'), (IV) or (V).

According to a specific embodiment, the invention is targeted at the compounds of formula (I) for which:
b=0 or 1, and
d=1 or 2,
and more particularly the compounds for which b+d≥2.

According to another specific embodiment, the invention is targeted at the compounds of formula (I) for which b+d≥2 and R and R' independently represent a hydrogen atom or an ethyl radical or one of their salts.

According to another specific embodiment of the invention, the invention is targeted at the compounds of formula (I) for which R and R' are identical and denote a hydrogen atom or an ethyl radical or one of their salts and is preferably targeted at the compounds of formula (I) for which R and R' denote a hydrogen atom or one of its salts.

According to an alternative form, the invention is targeted at the cosmetic use of at least one compound of formula (II):

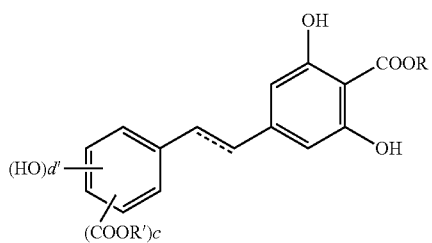

(II)

in which:

denotes a divalent radical chosen from a carbon-carbon single bond *—CH$_2$—CH—* or double bond *—CH=CH—*, of Z or E configuration and their mixtures, c=0 or 1, d'=1 or 2, it being understood that, if c=1, then the COOR' group is in the ortho position with respect to a phenol functional group, and R and R' independently denote a hydrogen atom, a linear C$_1$-C$_6$ alkyl radical or a branched C$_3$-C$_6$ alkyl radical, preferably a hydrogen atom, a linear C$_1$-C$_4$ alkyl radical or a branched C$_3$-C$_4$ alkyl radical, one of its stereoisomers and/or solvates and/or one of its salts, to treat and/or prevent signs of aging and/or of photoaging of keratinous substances, preferably the skin, and/or to depigment, lighten and/or whiten keratinous substances, preferably the skin.

Still in the context of this alternative form, and more preferably still, the choice will be made of the compounds for which R and R' independently denote a hydrogen atom or an ethyl radical or one of their salts.

Among the compounds of formula (II), the choice will more preferably be made of the compounds for which R and R' are identical and represent a hydrogen atom or an ethyl radical or one of their salts. More preferably still, the choice will be made of the compounds for which R and R' represent a hydrogen atom or one of its salts.

According to a specific embodiment of this alternative form, a subject matter of the invention is the cosmetic use of at least one compound of formula (II'):

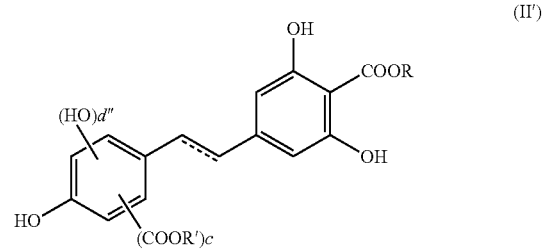

(II')

in which:

denotes a divalent radical chosen from a carbon-carbon single bond *—CH$_2$—CH$_2$—* or double bond *—CH=CH—*, of Z or E configuration or their mixtures, c=0 or 1, d"=0 or 1, it being understood that, if c=1, then the COOR' group is in the ortho position with respect to a phenol functional group, and R and R' independently denote a hydrogen atom, a linear C$_1$-C$_6$ alkyl radical or a branched C$_3$-C$_6$ alkyl radical, preferably a hydrogen atom, a linear C$_1$-C$_4$ alkyl radical or a branched C$_3$-C$_4$ alkyl radical, one of its stereoisomers and/or solvates and/or one of its salts, to treat and/or prevent signs of aging and/or of photoaging of keratinous substances, preferably the skin, and/or to depigment, lighten and/or whiten keratinous substances, preferably the skin.

Still in the context of this specific embodiment, and more preferably still, the choice will be made of the compounds for which R and R' independently denote a hydrogen atom or an ethyl radical or one of their salts.

Among the compounds of formula (II'), the choice will more preferably be made of the compounds for which R and R' are identical and represent a hydrogen atom or an ethyl radical or one of their salts. More preferably still, the choice will be made of the compounds for which R and R' represent a hydrogen atom or one of its salts.

Novel Compounds

As already indicated, the present invention also relates to the novel compounds of formulae (III), (IV) and (V), as defined above.

Compounds of Formula (III)

The compounds of formula (III) can also be defined as compounds of formula (I) for which:

b=1 and the phenol functional groups are in the meta position with respect to each other, d=2, and the divalent radical between the 2 aromatic rings is an unsaturated radical —CH=CH—, of Z or E configuration or their mixtures, preferably of E configuration.

According to a specific embodiment, the invention relates to the compounds of formula (III) in which R and R' independently denote a hydrogen atom, an ethyl radical or one of their salts.

According to an even more specific embodiment, the invention relates to the compounds of formula (III) in which R and R' are identical and represent a hydrogen atom or an ethyl radical or one of their salts. More preferably still, the choice will be made of the compounds for which R and R' represent a hydrogen atom or one of its salts.

Mention may in particular be made, among the compounds of formula (III), of the compounds Y, Z, Y', Y-Et, Z-Et and Y'-Et as defined below in table 1, one of their stereoisomers and/or solvates and/or one of their salts.

Another subject matter of the invention is more particularly a compound of formula (III) in which one of the phenol functional groups is in the para position with respect to the divalent radical —CH═CH—, namely one of formula (III'):

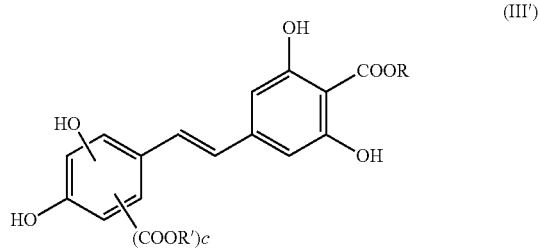

in which:

c=0 or 1, it being understood that, if c=1, then the corresponding COOR' functional group is in the ortho position with respect to a phenol functional group, and R and R' independently denote a hydrogen atom, a linear $C_1$-$C_6$ alkyl radical or a branched $C_3$-$C_6$ alkyl radical, preferably a hydrogen atom, a linear $C_1$-$C_4$ alkyl radical or a branched $C_3$-$C_4$ alkyl radical, one of its stereoisomers and/or solvates and/or one of its salts.

More preferably still, the choice will be made of the compounds for which R and R' independently denote a hydrogen atom or an ethyl radical or one of their salts.

Among the compounds of formula (III'), the choice will more preferably still be made of the compounds for which R and R' are identical and represent a hydrogen atom or an ethyl radical or one of their salts. More preferably still, the choice will be made of the compounds of formula (III') for which R and R' represent a hydrogen atom or one of its salts.

Mention may in particular be made, among the compounds of formula (III'), of the compounds Y, Z, Y', Y-Et, Z-Et and Y'-Et and as defined below in table I, one of their stereoisomers and/or solvates and/or one of their salts.

Compounds of Formula (IV)

The compounds of formula (IV) can also be defined as compounds of formula (I) for which:

b=1 and the two phenol functional groups are in the meta position with respect to each other, and the divalent radical between the 2 aromatic rings is a saturated radical —$CH_2$—$CH_2$—.

According to a specific embodiment of the invention, it is targeted at the compounds for which R and R' independently denote a hydrogen atom or an ethyl radical or one of their salts.

Among the compounds of formula (IV), the choice will more preferably be made of the compounds for which R and R' are identical and represent a hydrogen atom or an ethyl radical or one of their salts. More preferably still, the choice will be made of the compounds for which R and R' represent a hydrogen atom or one of its salts.

Mention may in particular be made, among the compounds of formula (IV), of the compounds X and X-Et as defined below in table I, one of their stereoisomers and/or solvates and/or one of their salts.

Compounds of Formula (V)

The compounds of formula (V) can also be defined as compounds of formula (I) for which:

b=1 and the two phenol functional groups are in the meta position with respect to each other, c=0, d=1 and the corresponding phenol functional group is in the para position with respect to the divalent radical, said divalent radical being an unsaturated radical —CH═CH—, and R is a linear $C_1$-$C_6$ alkyl radical or a branched $C_3$-$C_6$ alkyl radical, preferably a linear $C_1$-$C_4$ alkyl radical or a branched $C_3$-$C_4$ alkyl radical.

According to a specific embodiment of the invention, R denotes an ethyl radical.

Mention may in particular be made, among the compounds of formula (V), of the compound W-Et as defined below in table I, one of its stereoisomers and/or solvates.

The compounds of formula (I) in accordance with the invention can be collated in the following table I:

TABLE I

| Compound | Structure | Substructure |
|---|---|---|
| W | OH, $CO_2H$, OH, HO (Z and/or E) | Non-novel compound (described in *J. Mol. Catal. B: Enzymatic*, 2015, 122, 348) (I), (II), (II') |

TABLE I-continued

| Compound | Structure | Substructure |
|---|---|---|
| W-Et | [structure: 4-hydroxystyryl linked to 2,6-dihydroxybenzoic acid ethyl ester; Z and/or E] | Novel compound (I), (II), (II'), (V) |
| X | [structure: 4-hydroxyphenethyl linked to 2,6-dihydroxybenzoic acid] | Novel compound (I), (II), (II'), (IV) |
| X-Et | [structure: 4-hydroxyphenethyl linked to 2,6-dihydroxybenzoic acid ethyl ester] | Novel compound (I), (II), (II'), (IV) |
| Y | [structure: stilbene with 3-hydroxy-2-hydroxy-carboxylic acid substituent linked to 2,6-dihydroxybenzoic acid; Z and/or E] | Novel compound (I), (II), (III) and (III') |
| Y-Et | [structure: stilbene with 3-hydroxy-2-hydroxy-carboxylic acid ethyl ester substituent linked to 2,6-dihydroxybenzoic acid ethyl ester; Z and/or E] | Novel compound (I), (II), (III) et (III') |
| Y' | [structure: stilbene with 2,4-dihydroxyphenyl linked to 2,6-dihydroxybenzoic acid; Z and/or E] | Novel compound (I), (II), (III) et (III') |

TABLE I-continued

| Compound | Structure | Substructure |
|---|---|---|
| Y'-Et | 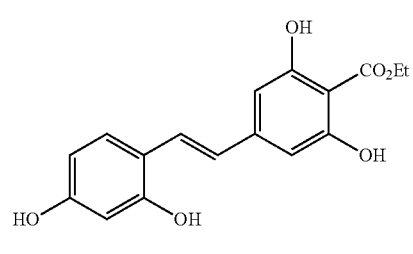  Z and/or E | Novel compound (I), (II), (III) et (III') |
| Z | 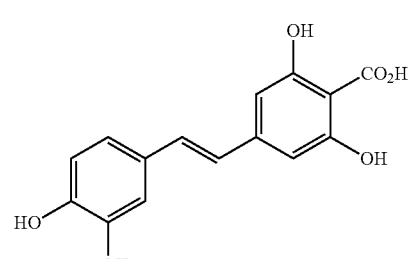  Z and/or E | Novel compound (I), (II), (III) et (III') |
| Z-Et | 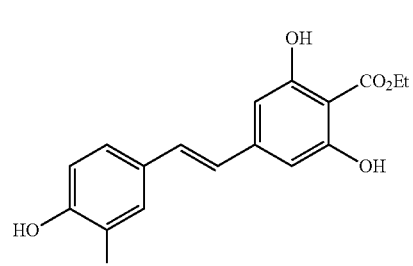  Z and/or E | Novel compound (I), (II), (III) et (III') | and also their salts and/or solvates and/or stereoisomers.

According to a specific embodiment of the invention, the invention is more particularly targeted at the cosmetic use of the compound W as described above, of one of its salts, solvates and/or isomers, more particularly still for the purpose of decreasing and/or delaying the signs of aging of keratinous substances, and in particular of the skin, and/or also for the purpose of depigmenting and/or lightening and/or whitening the skin.

The compounds in accordance with the present invention can be prepared according to the processes and schemes described below.

The compounds corresponding to the formula (I) can be prepared from the corresponding polyphenols (A-I), for which b and d are as defined above, in one stage (carboxylation) if R=H or 2 stages (carboxylation and then esterification) if R=alkyl, according to the following Scheme 1.

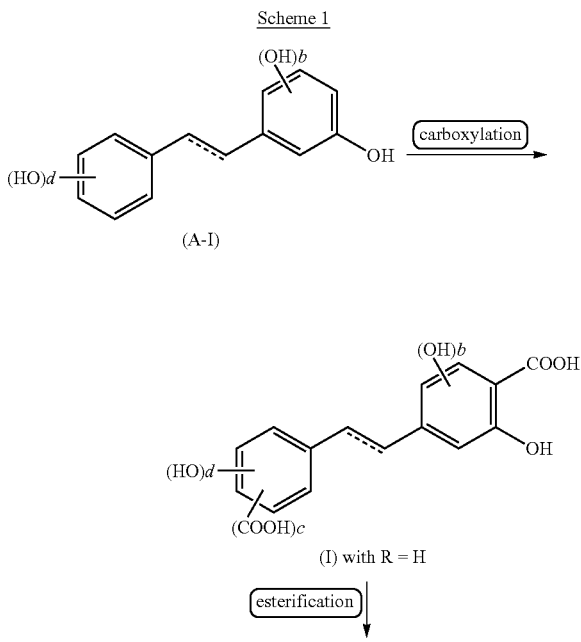

Scheme 1

-continued

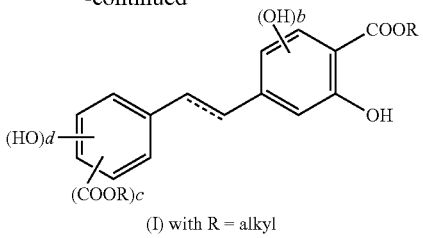

(I) with R = alkyl

The carboxylation (monocarboxylation or multicarboxylation) reaction can, for example, be a carboxylation biocatalyzed by an enzyme of decarboxylase type, such as:

the decarboxylase isolated from *R. radiobacter*, the decarboxylase specific for 2,3-dihydroxybenzoic acid isolated from *Aspergillus oryzae*, the decarboxylase specific for 2,6-dihydroxybenzoic acid isolated from *Rhozobium* sp., and the decarboxylase specific for salicylic acid isolated from *Trichosporon moniliiforme*.

The enzymes can be used in isolated form (as described, for example, in M. Sato et al., "Enzymatic carboxylation of hydroxystilbenes by the γ-resorcylic acid decarboxylase from *Rhizobium radiobacter* WU-0108 under reverse reaction conditions", *J. Mol. Catal. B: Enzymatic*, 2015, 122, 348) or else in the form of lyophilized whole cells, as described, for example, in C. Wuensch et al., "Regioselective 1 ortho-carboxylation of phenols catalyzed by benzoic acid decarboxylases: a biocatalytic equivalent to the Kolbe-Schmitt reaction", *RSC Adv.*, 2014, 4, 9673, according to Scheme 2 which follows.

Scheme 2

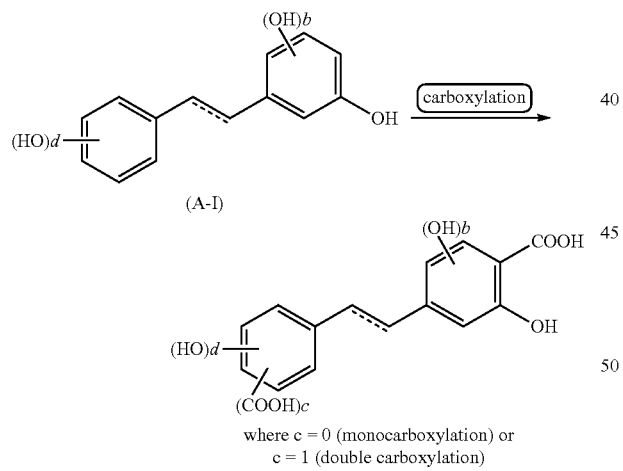

where c = 0 (monocarboxylation) or
c = 1 (double carboxylation)

The compound (A-I), in solution in water or in an organic solvent (such as methanol, ethanol, tetrahydrofuran, acetonitrile, ethyl acetate, isopropanol, t-butanol, 1,6-dioxane, butan-1-ol, acetone, butanone, toluene, 2-methyltetrahydrofuran, n-heptane, cyclohexane, t-butyl methyl ether) or in a water/organic solvent mixture, can be added to a buffer solution at slightly acidic pH, for example a phosphate buffer at pH 5-7, containing the enzyme or the whole cells (in a concentration of 0.5-50 mg/ml). The concentration of the substrate can be adjusted to between 1 mM and 1M.

This mixture can subsequently be added to a 1-5M aqueous potassium hydrogencarbonate $KHCO_3$ solution.

The flask containing the reaction medium can be sealed and stirred at 10-70° C. for 1 to 48 hours.

The reaction can be interrupted by addition of a strong acid, for example HCl, until a pH of 0-3 is obtained. The aqueous phase thus obtained can be extracted several times using an organic solvent, such as diethyl ether, ethyl acetate or dichloromethane. The organic phases can be combined and dried over sodium sulfate. The solvents can be evaporated under reduced pressure and the residue can be purified by silica gel column chromatography.

The esterification reaction can be carried out according to the methods known to a person skilled in the art for the esterification of derivatives of salicylic acid type.

The intermediate to be esterified, in solution in the alcohol ROH, can be heated at reflux in the presence of an inorganic acid, such as, for example, HCl or $H_2SO_4$, for 1 to 24 hours. After returning to ambient temperature, the reaction medium can be diluted by addition of water (1-10 volumes) and the product can be extracted several times using an organic solvent, such as diethyl ether, ethyl acetate or dichloromethane. The organic phases can be combined and dried over sodium sulfate. The solvents can be evaporated under reduced pressure and the residue can be purified by silica gel column chromatography.

More particularly, the compounds of formulae (III) and (IV) can be prepared according to the method described below.

The compounds of formula (III), respectively (IV), can be prepared by carboxylation of the precursors (A-III), for which d and c are as defined above, respectively (A-IV), for which d and c are as defined above, according to the same method as for the preparation of (I) from (A-I), according to the following Schemes 3 and 4:

Scheme 3

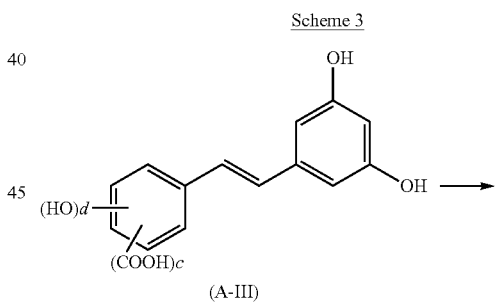

(A-III)

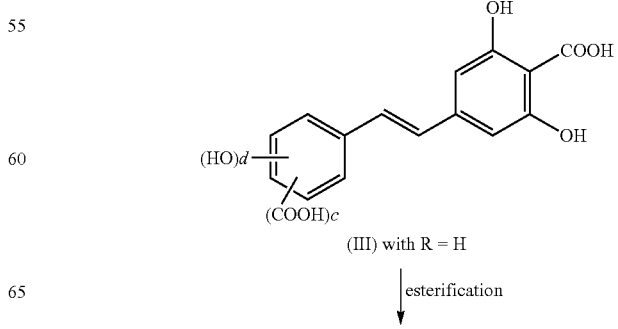

(III) with R = H

↓ esterification

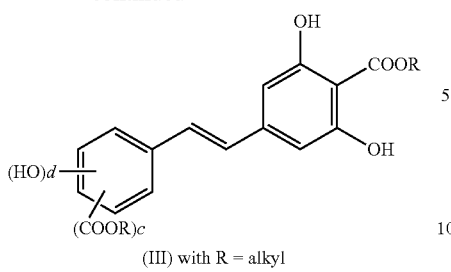

(III) with R = alkyl

During the preparation of a compound of formula (III), the first stage as reported above in Scheme 3 can give rise to the formation of a compound of following formula (VI):

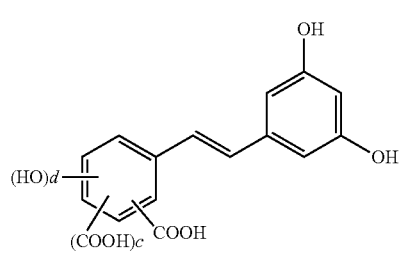

Among these compounds of formula (VI), in which d and c are as defined above, the following compounds, for which d=2 and c=0, are novel. Their preparation is illustrated in example 2 below.

Scheme 4

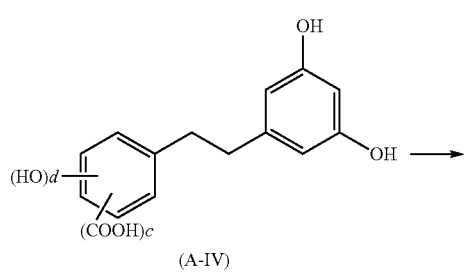

(A-IV)

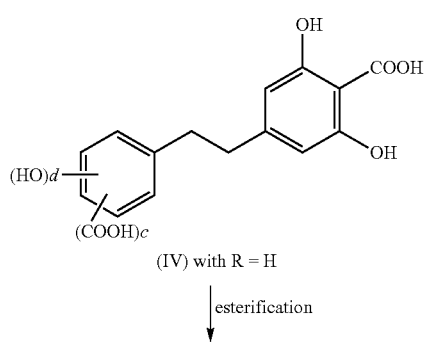

(IV) with R = H

↓ esterification

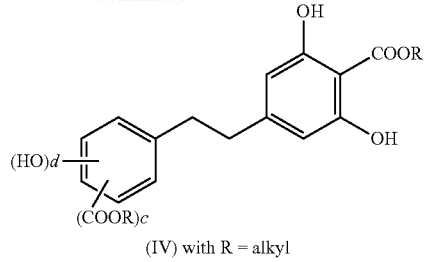

(IV) with R = alkyl

With regard to them, the compounds of formula (V) can be prepared by esterification of the compound (W) according to the method described for the preparation of (I), according to the following Scheme 5:

Scheme 5

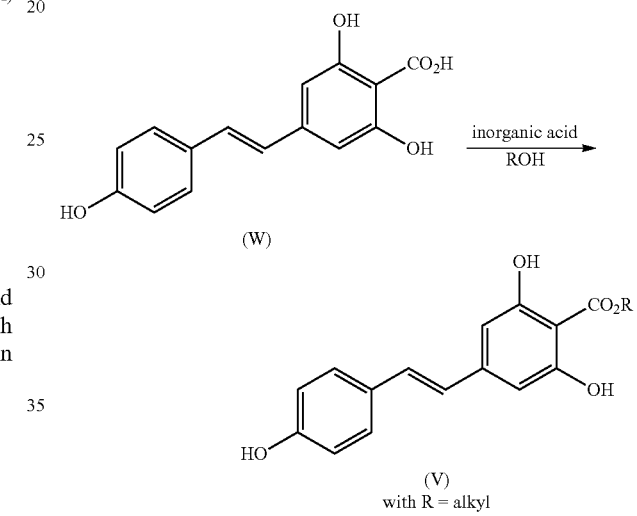

(V) with R = alkyl

Cosmetic Composition

A composition suitable for the invention, namely intended for the implementation of the invention, can be a cosmetic composition, and thus comprises a physiologically acceptable medium.

"Physiologically acceptable medium" is understood to mean a medium compatible with keratinous substances, such as the skin, or any other cutaneous region of the body, of the face, of the armpits in particular, or also as are defined above. A physiologically acceptable medium is preferably a cosmetically acceptable medium, that is to say a medium devoid of unpleasant odor, color or appearance, and which is completely compatible with the topical administration route.

By way of example, a cosmetic composition used according to the present invention comprises an amount of between 0.001% and 30% by weight, preferably between 0.01% and 10% by weight, in particular between 0.5% and 5% by weight, with respect to the total weight of the composition, of at least one compound of formula (I), (II), (II'), (III), (III'), (IV) or (V), its salts, solvates and/or stereoisomers.

The composition in accordance with the invention is intended for a topical application.

The composition can additionally comprise any constituent normally employed in the envisaged application.

Mention may in particular be made of water, solvents, oils of mineral or organic origin, waxes, pigments, fillers, surfactants, additional cosmetic active agents other than the compounds of formula (I), (II), (II'), (III), (III'), (IV) or (V), or also polymers. For example, the composition according to the invention can comprise at least one cosmetic adjuvant chosen, for example, from water; organic solvents, in particular $C_2$-$C_6$ alcohols and $C_2$-$C_{10}$ carboxylic acid esters, hydrocarbon oils, silicone oils, fluorinated oils, waxes, pigments, fillers, dyes, surfactants, emulsifiers, UV-screening agents, film-forming polymers, hydrophilic or lipophilic gelling agents, thickeners, preservatives, fragrances, bactericides and odor absorbers.

According to a specific form of the invention, the composition in accordance with the invention can additionally also contain one or more deodorant active agents and/or one or more antiperspirant active agents.

In the composition according to the invention, the compounds (I), (II), (II'), (III), (III'), (IV) and/or (V) can also be used together with additional antiaging or photoprotective active agents other than the compounds of formulae (I), (II), (II'), (III), (III'), (IV) and/or (V).

In the composition according to the invention, the compounds (I), (II), (II'), (III), (III'), (IV) and/or (V) can also be used together with additional depigmenting active agents other than the compounds of formulae (I), (II), (II'), (III), (III'), (IV) and/or (V).

The composition according to the invention can also comprise at least one additional cosmetic active agent other than the compounds of formulae (I), (II), (II'), (III), (III'), (IV) and/or (V), such as, for example, desquamating agents, moisturizing agents, NO-synthase inhibitors, dermo-decontracting agents, tightening agents, and their mixtures.

Thus, the composition according to the invention can be provided in the form of an antiaging composition, in particular a care composition, intended to combat external signs of skin aging, and/or in the form of a photoprotective composition and/or in the form of a depigmenting composition.

This composition can be provided in any formulation form normally used in the cosmetics field; it can in particular be in the form of an optionally gelled aqueous solution, of a dispersion of the optionally two-phase lotion type, of an emulsion obtained by dispersion of a fatty phase in an aqueous phase (O/W) or vice versa (W/O), or of a triple (W/O/W or O/W/O) emulsion or of a vesicular dispersion of ionic and/or nonionic type.

The composition of the invention can constitute, for example, a lotion, a gel, a cream or a milk, or also a stick, indeed even an aerosol.

Thus, the composition can comprise any constituent normally employed in the topical application and administration envisaged.

Of course, a person skilled in the art will take care to choose this or these optional additional compounds, and/or their amounts, such that the advantageous properties of the compound of formula (I), (II), (II'), (III), (III'), (IV) or (V) used according to the invention are not, or not substantially, detrimentally affected by the envisaged addition and such that the properties of the compositions resulting therefrom are compatible with the topical route.

A composition according to the invention can have the form of a care or makeup product for the face and/or body, and be packaged, for example, in the cream form in a jar or fluid form in a tube or in a pump-action spray.

According to a preferred embodiment, a composition according to the invention comprising at least one compound of formula (I), (II), (II'), (III), (III'), (IV) or (V) of the invention is formulated in an antiaging cream and/or in a cream for photoprotection and/or a cream for depigmentation, indeed even a stick.

A composition according to the invention can be manufactured by any known process generally used in the cosmetics field.

Cosmetic Methods

The present invention also relates to a method for the nontherapeutic cosmetic treatment of keratinous substances, in particular of the skin, comprising the application, to said keratinous substances, of a composition as defined according to the invention.

In some embodiments of this method, the composition is applied to mature and/or wrinkled skin.

In some embodiments of this method, the composition is applied to the skin of people who wish overall to lighten the complexion or flesh tone of their skin.

In some embodiments of this method, the composition is applied to skin exhibiting brownish pigmentation blemishes or blemishes due to aging or to the skin of individuals desiring to combat the appearance of a brownish color originating from melanogenesis.

The nontherapeutic cosmetic method of the invention is performed by topically administering a composition in accordance with the invention.

The topical administration consists of the external application, to the keratinous substances, in particular the skin, of cosmetic compositions according to the usual technique for using these compositions.

By way of illustration, the cosmetic method according to the invention can be performed by application, for example daily, of a composition in accordance with the invention, which can be formulated, for example, in the form of a cream, gel, serum, lotion, emulsion, makeup-removing milk or after sun composition.

According to another embodiment, the application is repeated, for example from 1, 2 to 3 times daily for one day or more and generally for an extended period of at least 4 weeks, indeed even 4 to 15 weeks, indeed even more, with, if appropriate, one or more periods of stoppage.

According to a specific form of the invention, other agents intended to make the appearance and/or the texture of the skin more attractive may also be added to the composition according to the invention.

The present invention also relates to the nontherapeutic use of a cosmetic composition as defined above, for cosmetically preventing and/or treating signs of skin aging and/or for providing a photoprotective effect, such as an antioxidant effect.

The present invention also relates to the nontherapeutic use of a cosmetic composition as defined above, for cosmetically preventing and/or treating blemishes due to aging, for depigmenting the skin and/or for whitening it and/or for lightening it.

The invention also relates to the nontherapeutic use of a composition as defined in the present description, for improving the firmness of the skin.

Throughout the description, the expression "comprising a" should be understood as being synonymous with "comprising at least one", unless otherwise specified.

The expressions "between . . . and . . . ", "of between . . . and . . . " and "ranging from . . . to . . . " should be understood as meaning limits included, unless otherwise specified.

The examples which follow are presented as nonlimiting illustrations of the invention.

EXAMPLES

Example 1: Preparation of Compound X

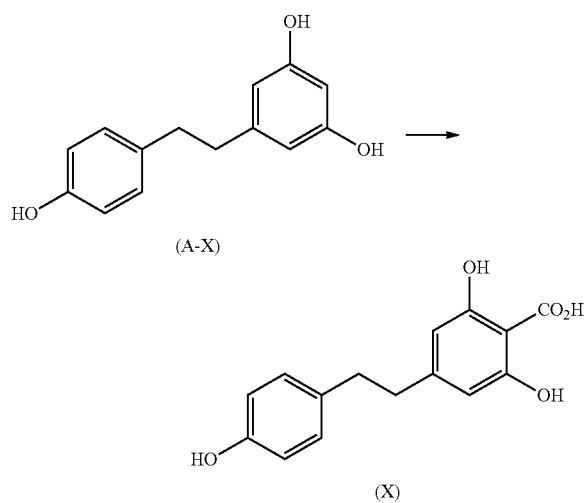

The substrate (A-X), in solution in methanol (50 mg in 1 ml), is added to 19 ml of a phosphate buffer solution at pH 5.5 containing the whole cells (651 mg, producing the decarboxylase specific for 2,6-dihydroxybenzoic acid isolated from *Rhozobium* sp.). This mixture is subsequently added to a 3M aqueous potassium hydrogencarbonate $KHCO_3$ solution. The flask containing the reaction medium is sealed and stirred at 30° C. for 24 hours.

The reaction is interrupted by addition of a 6M aqueous HCl solution, until a pH of 2 is obtained. The aqueous phase thus obtained is extracted 4 times with ethyl acetate (10 ml). The organic phases are combined and dried over sodium sulfate. The solvent is evaporated under reduced pressure and the residue is purified by silica gel column chromatography (dichloromethane/methanol: 90/10), to result in the product (X) in the form of an offwhite/yellow solid (yield: 45%).

The $^1$H NMR spectrum and the mass spectrum are in accordance with the expected structure.

Example 2: Preparation of the Compounds Y and Y'

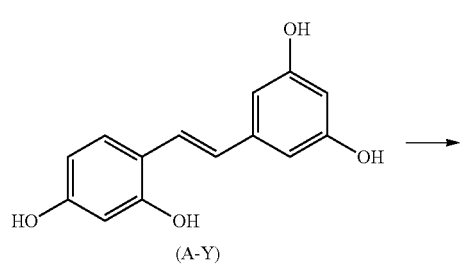

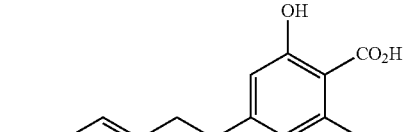

Oxyresveratrol (A-Y), in solution in methanol (50 mg in 1 ml), is added to 19 ml of a phosphate buffer solution at pH 5.5 containing the whole cells (651 mg, producing the decarboxylase specific for 2,6-dihydroxybenzoic acid isolated from *Rhozobium* sp.). This mixture is subsequently added to a 3M aqueous potassium hydrogencarbonate $KHCO_3$ solution. The flask containing the reaction medium is sealed and stirred at 30° C. for 24 hours.

The reaction is interrupted by addition of a 6M aqueous HCl solution, until a pH of 2 is obtained. The aqueous phase thus obtained is extracted 4 times with ethyl acetate (10 ml). The organic phases are combined and dried over sodium sulfate. The solvent is evaporated under reduced pressure. The crude reaction product thus obtained corresponds to the mixture of (Y), (Y') and (Y"):

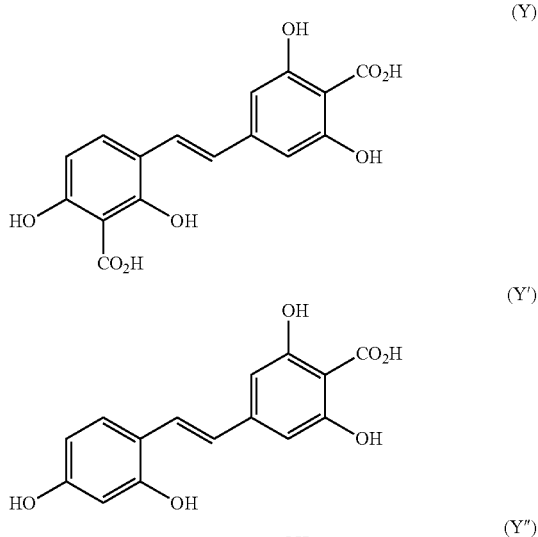

The residue is purified by silica gel column chromatography (dichloromethane/methanol: 90/10), to isolate the product (Y) in the form of an offwhite/yellow solid (yield: 66%).

The $^1$H NMR spectrum and the mass spectrum are in accordance with the expected structure.

Example 3: Demonstration of the Depigmenting Activity

The effectiveness was demonstrated on the basis of the following test:

The evaluations of the effect of prevention of or of decrease in the pigmentation of the skin and/or of lightening of the latter can be carried out in the following way.

The measurement of the depigmenting activity (reduction in the production of melanin) of compounds of formula (I) was performed by assaying the melanin produced by normal human melanocytes in vitro as follows.

First of all, normal human melanocytes are cultured and dispensed into 384 wells. After 24 hours, the culture medium was replaced with a medium containing compounds of formula (I) to be evaluated. The cells were incubated for 72 hours before measurement of the final optical density, which measures the amount of melanin produced by the melanocytes. A close effect is performed using a wide concentration range of the compounds evaluated. Thus, by making the concentrations and the measurements of melanin correspond, it is possible to determine an IC50 in µM: concentration at which 50% decrease in melanin synthesis is achieved.

The compound W was in particular tested and showed a depigmenting effect.

Thus, the compound W shows an inhibiting effect on the production of melanin with an IC50 value of 25 µM, without cytotoxicity in the concentration range tested. The measurements at the different concentrations are collated in table II below.

TABLE II

| Concentration | Mean percentage Depigmentation | Percentage Standard deviation |
|---|---|---|
| 0.0002 | 125.6 | 4.6 |
| 0.0001 | 99.7 | 1.1 |
| 0.00005 | 76.7 | 2.9 |
| 0.000025 | 43.0 | 3.7 |
| 0.0000125 | 32.8 | 6.2 |
| 0.00000625 | 22.8 | 4.1 |
| 0.000003125 | 15.6 | 2.0 |
| $1.5625 \times 10^{-6}$ | 9.7 | 1.7 |
| $7.8125 \times 10^{-7}$ | 5.5 | 4.3 |
| $3.90625 \times 10^{-7}$ | −0.9 | 2.9 |

Example 4: Demonstration of the Anti-Aging Activity

The effectiveness was demonstrated on the basis of the following tests:

The evaluations of the effect of activation of hyaluronic acid (HA) biosynthesis can be carried out in the following ways.

Gene Markers Expression

Human epidermal keratinocytes were seeded in 48 well-culture plate and cultured for 48 hours at 37° C. and 5% of $CO_2$ in culture medium with renewal of culture medium after the first 24 hours. At the end of incubation, culture medium was replaced by assay medium containing or not (control) raw material and cells were incubated for additional 24 hours. All experimental conditions were performed in n=3. At the end of treatment, cells were washed twice in PBS (w/o $CaCl_2$, w/o $MgCl_2$) and RNA extraction was performed using MagMAX™-96 Total RNA Isolation Kit (Ambion cat n° AM8130) according to manufacturer recommendation. RNA quantification and quality control were performed using Labchip GX (Perkin Elmer). Relative expression of selected markers was measured by two steps RT-qPCR. In a first step, a reverse transcription was performed using the Quantitect® Reverse transcription kit (QIAGEN) and according to manufacturer recommendation. Then, PCR experiments were performed using a LightCycler® 480 Real-Time PCR System measuring SYBR®Green incorporation (Roche).

The compound W was in particular tested and showed an effect on HAS3 expression. Indeed, the compound W is able to increase the expression of the HAS3 marker without cytotoxicity at 30 µM, with a fold change of 2.45 vs control. The measurements are collated in table III and figure I below.

TABLE III

| Treatment | Concentration | Relative expression (UA) | Fold change (Nb) | Mean | sd | p (vs control) |
|---|---|---|---|---|---|---|
| Control | — | 1.34E−03 | 0.9449488 | 1.00 | 0.06 | — |
|  |  | 1.40E−03 | 0.99192853 |  |  |  |
|  |  | 1.50E−03 | 1.06312267 |  |  |  |
| Compound W | 30 µM | 3.61E−03 | 2.55336543 | 2.45 | 0.10 | 4.11E−03 |
|  |  | 3.44E−03 | 2.43243293 |  |  |  |
|  |  | 3.32E−03 | 2.34957534 |  |  |  |

Thus, compound W is able to stimulate the expression of the HAS3 marker by keratinocytes, which is the gene coding for hyaluronic acid synthase. Hence, since hyaluronic acid is an important constituent of extracellular matrix, playing major role for instance in mechanical properties of dermis, compound W has thus been proven as improving skin firmness, and more largely as showing anti-aging effect.

Example 5: Example of Composition in Accordance with the Invention

The percentages of compounds shown are percentages by weight, with respect to the total weight of the composition in which they are present.

| | |
|---|---|
| Compound W | 1% |
| Carbomer (Carbopol 981 from Lubrizol) | 1% AM |
| Preservatives | q.s. |
| Water q.s. for | 100% |

AM: Active material

The above composition, applied topically to the skin, makes it possible to attenuate brown blemishes.

The invention claimed is:
1. A compound of formula (III):

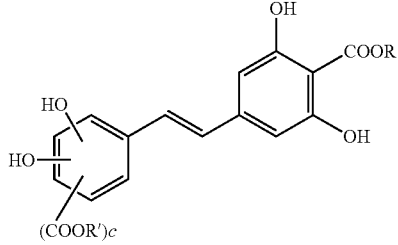

(III)

wherein:
c=0 or 1,
with the proviso that, if c=1, then the COOR' group is in the ortho position with respect to a phenol functional group, and
R and R' are each independently a hydrogen atom, a linear $C_1$-$C_6$ alkyl radical or a branched $C_3$-$C_6$ alkyl radical, one of its stereoisomers and/or solvates and/or one of its salts.

2. A compound of formula (III'):

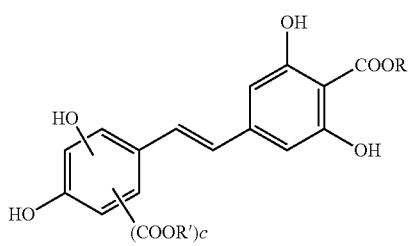

(III')

wherein:
c 0 or 1,
with the proviso that, if c=1, then the corresponding carboxylate functional group is in the ortho position with respect to a phenol functional group, and
R and R' are each independently a hydrogen atom, a linear $C_1$-$C_6$ alkyl radical or a branched $C_3$-$C_6$ alkyl radical one of its stereoisomers and/or solvates and/or one of its salts.

3. A compound selected from the group of compounds consisting of Y, Y-Et, Y', Y'-Et, Z and Z-Et, one of its stereoisomers and/or solvates and/or one of its salts, the configuration being Z or E:

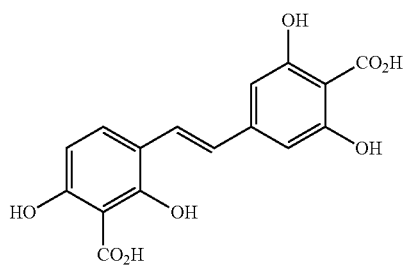

(Y)

Z and/or E

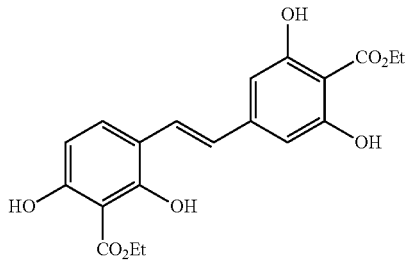

(Y-Et)

Z and/or E

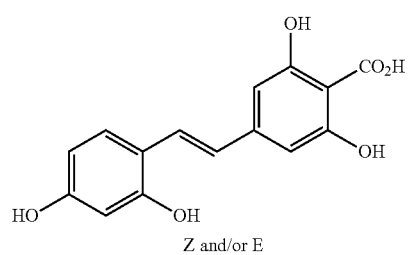

(Y')

Z and/or E

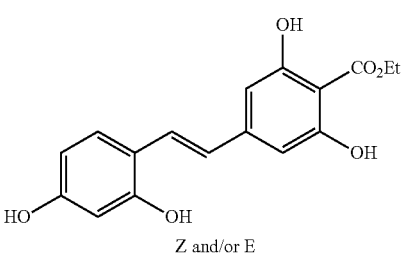

(Y'-ET)

Z and/or E

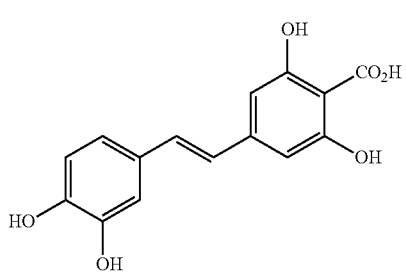

(Z)

Z and/or E

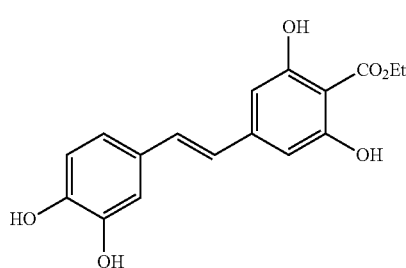

(Z-Et)

Z and/or E

4. A compound of formula (IV):

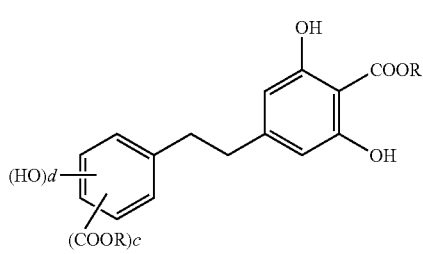

wherein:
c=0 or 1,
d=0, 1 or 2,
with the proviso that, if c=1, then d≥1 and the COOR' group is in the ortho position with respect to a phenol functional group, and
R and R' are each independently a hydrogen atom, a linear $C_1$-$C_6$ alkyl radical or a branched $C_3$-$C_6$ alkyl radical, one of its stereoisomers and/or solvates and/or one of its salts.

5. A compound selected from the compounds X and X-Et, one of its stereoisomers and/or solvates and/or one of its salts, the configuration being Z or E

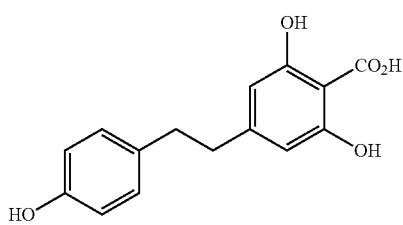

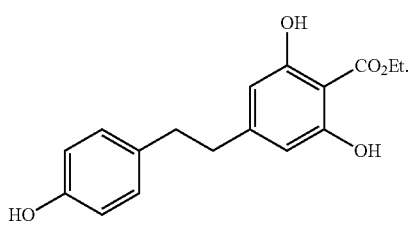

6. A compound of formula (V):

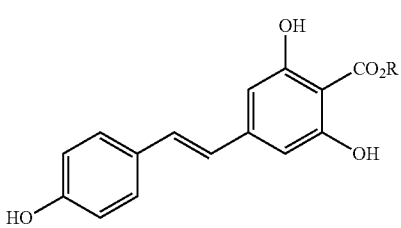

wherein:
R is a linear $C_1$-$C_6$ alkyl radical or a branched $C_3$-$C_6$ alkyl radical, one of its stereoisomers and/or solvates and/or one of its salts.

7. A compound W-Et, one of its stereoisomers and/or solvates, the configuration being Z or E

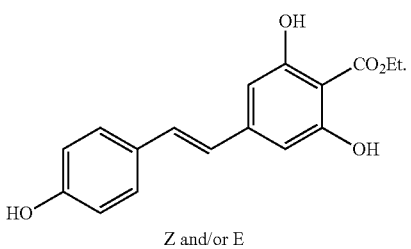

Z and/or E

8. A composition, comprising, in a physiologically acceptable medium, at least one compound of formula (III), as defined in claim 1.

9. A composition comprising, in a physiologically acceptable medium, at least one compound of formula (III') as defined in claim 2.

10. A composition comprising, in a physiologically acceptable medium, at least one compound of formula (IV) as defined in claim 4.

11. A composition comprising, in a physiologically acceptable medium, at least one compound of formula (V) as defined in claim 6.

* * * * *